United States Patent [19]

Wilson

[11] Patent Number: 4,649,049

[45] Date of Patent: Mar. 10, 1987

[54] RABIES VACCINE

[75] Inventor: Jan S. Wilson, Fort Dodge, Iowa

[73] Assignee: American Home Products Corporation, New York, N.Y.

[21] Appl. No.: 629,307

[22] Filed: Jul. 10, 1984

[51] Int. Cl.$^4$ ............................................. A61K 39/205
[52] U.S. Cl. ........................................ 424/89; 424/88; 435/235; 435/238
[58] Field of Search ................. 424/88, 89; 514/2, 21; 435/235, 238, 948; 260/112 R

[56] References Cited

U.S. PATENT DOCUMENTS 4,252,792  2/1981  Blades .................................... 424/89
4,584,194  4/1986  Bass et al. ............................. 424/89

FOREIGN PATENT DOCUMENTS 8504810  11/1985  PCT Int'l Appl. ................... 424/89

OTHER PUBLICATIONS

CA. No. 1190x, vol. 75, 1971, Substitution of HEPES for Bicarbonate . . . Cells, Melzon et al.
CA. No. 74524a, vol. 85, 1976, The Effects of HEPES Buffer . . . Thrombokinase, Roberts.

Primary Examiner—John Kight
Assistant Examiner—Garnette D. Draper
Attorney, Agent, or Firm—Adley F. Mandel

[57] ABSTRACT

A rabies vaccine composition is disclosed which comprises a sterilized suspension of proteineous suckling mice or rat brain particles of injectable particle size laden with an amount of inactivated rabies virus which is equivalent to a virus titer of at least $10^{5.0}$ to about $10^6$ $MLD_{50}$ per 0.1 milliliter thereof at a brain tissue concentration of from about 0.3% to about 5.0% by weight, in physiological buffer solution having a pH of between about 7.5 and about 8.0 and comprising an amount dissolved therein, of between 0.02 and 0.08, preferably 0.04, moles per liter, of a buffer composition comprising a mixture of an organic base formula

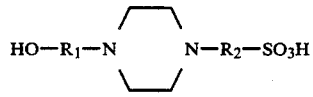

wherein $R_1$ and $R_2$ each are $CH_2$, $C_2H_4$ or $C_3H_6$, preferably $C_2H_4$ combined with between 0.03 and 0.12, preferably 0.06 moles per liter of its corresponding salt, preferable sodium salt. The presence of ethylene maleic anhydride enhances the effectiveness of the composition. The vaccine composition exhibits a high potency and its pH value remains stable over a prolonged period of time.

15 Claims, No Drawings

RABIES VACCINE

This invention relates to an improved method of preparing a rabies vaccine cultured in suckling mouse or rat brain tissue and to the product vaccine.

More particularly this invention relates to a rabies vaccine of murine origin utilizing N-2-hydroxyethylpiperazine-N-2-ethanesulfonic acid as a buffer and ethylene maleic anhydride as an adjuvant.

BACKGROUND OF THE INVENTION

It is known that a high antigenic mass rabies virus can be propagated in suckling mouse brain or rat brain tissue and that standardized vaccine preparations can be prepared with rabies virus propagated in this manner. Generally, vaccine production quantities of a high antigenic mass rabies virus were propagated in suckling mouse or rat brain tissue starting with any of the strains of rabies virus generally available for this purpose. The CVS strain of rabies virus are known to be effective for use in such propagation and are available from the National Institute of Health, Bethesda, Md., as well as from other Culture Depositories. They may be obtained as a lyophilized suspension, which when reconstituted, has a virus titer between about $10^6$ and $10^7 MLD_{50}$ per 0.03 ml. A master seed virus may be prepared from such a suspension when intracerebrally inoculated into suckling mice or rats and the brains recovered after propagation. This was accomplished by techniques known in the art. For example, harvested suckling mice were cooled to 4° C. or held at a temperature of between about −40° and −60° C. after the virus incubation period and prior to processing. The frozen mice were thawed just prior to harvest and the rabies virus laden brain tissue removed, generally, at or near 4° C. temperature. Following the processing the rabies virus laden brain were suspended in a suitable medium and stored at a temperature between about −40° and −60° C.

When the first batch of processed viral laden brain tissue was used as a master seed, the same was, typically, suspended in a suitable media at a concentration of about 1-10% horse serum and containing antibiotics. The master seed had a virus titer of at least $10^{7.0} MLD_{50}$ per 0.01 ml at a 10% concentration to insure high potency.

When the first batch of harvested viral laden brain tissue was to be used as a master seed, it was subjected to high shear agitation so as to reduce the particle size of the suspended brain tissue to between about 1 and 10 microns. This was accomplished by subjecting the suspension to high shear agitation at a relatively high concentration of at least about 20 percent by weight (wt %) and thereafter diluting the same to the desired concentration for storage. The master seed was stored, thawed and used, as required, for subsequent testing and/or the production of working seed.

After a first batch of viral laden brain tissue was prepared, all subsequent batches of brain tissue containing the living, fully virulent rabies virus were produced by inoculating suckling mice or rats with viral laden brain tissue. A suckling mouse received a dose suitably sufficient for inducing rabies having a strength of between about 100 and $500MLD_{50}$. Generally, this was achieved with a dose of about 0.01 ml, although other size doses could be used.

The batch used as the primary master seed would normally be tested for purity, safety, potency, sterility, and identity while subsequent batches of viral laden brain tissue would be tested only for purity, safety, and potency. Both the purity and sterility tests may be accomplished in accordance with procedures set forth in Title 9 of the Federal Regulations. Safety may be determined by intracerebrally inoculating any of several animal species with the inactivated virus and observing the inoculated species for a period of about 21 days. Identity may be determined by inoculating guinea pigs and or mice intracerebrally and observing the development of typical rabies symptoms; in cell cultures by fluorescent antibody microscopy, using specific fluorescein labeled rabies antiserum; and by the virus ability, when inactivated, to protect guinea pigs and/or mice against lethal challenge of rabies virus. Potency may be determined by inoculating any of several animal species, in accordance with known procedures, with a vaccine containing the inactivated virus and determining the minimum concentration or dose required to protect the species thus inoculated. Generally, all tests may be completed in accordance with procedures well known in the prior art and all may be completed on the suckling mice or rats used to prepare the master seed and routinely accomplished thereafter.

As is known in the prior art, the suckling mouse brain tissue cannot effectively be separated from the living, fully virulent rabies virus propagated therein without reducing the virus titer of the resulting viral suspension to an unsatisfactory level. For this reason, the brain tissue is retained in the vaccine of the present invention. Tests show that there is no reaction to the presence of brain tissue in the vaccine.

The prior art rabies vaccines have typically contained 3 to 5 or more percent by weight of brain tissue. This resulted in an inelegant appearance of the dosage form due to settling out of brain tissue. The known vaccines have a maximum virus titer of about $10^5MLD_{50}$ per 0.01 ml at a concentration of 3 percent by weight for a one year vaccine and about $10^7MLD_{50}$ per 0.01 ml at a concentration of 6 percent by weight for a three year vaccine. The known vaccines have a median antibody titer at one month of about 1:512. The median antibody titer of known rabies vaccines is about 1:146 one year after administration and about 1:6 three years after administration. A recent patent is U.S. Pat. No. 4,252,792 directed to a rabies vaccine using tris (hydroxymethyl-)amino methane(TRIS) and its hydrochloride as a buffer and Carbopol as an adjuvant.

It is an object of this invention to provide a rabies vaccine which produces an improved antibody response.

It is another object of this invention to provide a rabies vaccine which has an improved antibody concentration at the end of the nominal period of immunity.

It is another object of the present invention to provide rabies vaccine of murine origin which utilizes greatly reduced amounts of cell tissue per dose.

It is a further object of the present invention to provide a rabies vaccine which yields more doses per unit of culture tissue.

It is yet another object of the invention to provide a pharmaceutically elegant dose form.

It is a further object of the invention to provide a more economical process for making rabies vaccine.

Other and further objects will be apparent to those skilled in the art from reading the following description of the invention.

It has been found that an improved rabies vaccine may be prepared which uses substantially less mouse brain culture in each dose to achieve equal or superior protection. Typically the vaccine of the present invention contains about 1.2 percent by weight of mouse brain tissue whereas the prior art vaccines contained about 5 percent by weight.

One result of this discovery is that more doses can be made from the same amount of tissue. In turn this reduces the cost of preparing the unit dose of vaccine.

Another result of this discovery is that the use of less brain tissue results in a cosmetically better appearing dose form. This results in part from the elimination of settling out of heavy tissue particles.

Surprisingly, it has also been found that the vaccine of the present invention produces a greater antibody response evidenced by a higher titer.

Also surprisingly it has been found that the antibody concentration at the end of the nominal period of protection is greater. This provides improved protection during the nominal period and extends immunity beyond the nominal duration of immunity.

It has been found that a known buffer system when used as defined below, not only acts as a buffer but unexpectedly has a potentiating effect on the antibody titers and results in a markedly improved rabies vaccine.

The objects of the present invention may be achieved with a rabies vaccine composition comprising a sterilized suspension of proteinous suckling mouse brain particles of injectable particle size laden with an amount of inactivated rabies virus which is equivalent to a virus titer of about $10^5$ to about $10^6$ MLD$_{50}$ per 0.1 milliliter thereof at a brain tissue concentration of about 0.3 to about 5% by weight, in an aqueous buffer solution having a pH of between about 7.5 and about 8.0 and containing between 0.02 and 0.08, preferably 0.04 moles per liter of a dissolved buffer composition comprised of an organic base of the formula

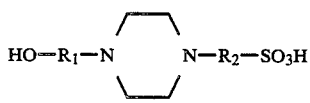

wherein $R_1$ and $R_2$ are $CH_2$, $C_2H_4$ or $C_3H_6$, combined with between 0.03 and 0.12, preferably 0.06 moles per liter, any of its acid addition salts which are compatible with virus replication. The preferred buffer composition is N-2-hydroxyethylpiperazine-N-2-ethanesulfonic acid (hereinafter HEPES) and its organic and inorganic acid addition salts.

Both HEPES and HEPES salt are commercially available from Research Organics, Cleveland, Ohio, U.S.A., and are identified by the trademark "HEPES."

The suitable organic and inorganic acid addition salts include sodium salts, hydrochlorides, carbonates, nitrates, acetates, benzoates, maleates, oxalates, and succinates. Most preferred is a mixture of N-2-hydroxyethylpiperazine-N-2-ethanesulfonic acid and its sodium salt. The ratio between the free base and its salts within the above buffer composition will vary depending on the desired pH-value in the vaccine composition and the particular buffer substances which are used. For example, in order to achieve a pH-value of between 7.5 and 8.0 at a temperature of about 25° C., a weight ratio of HEPES/HEPES salt of between about 1.0/1.0 and about 1.0/4.0 is suitable.

Preferably the vaccine composition is buffered to a pH-value of between about 7.5 to 8.0, and most preferably to a pH-value of about 7.7 at a temperature of about 25° C. Accordingly, the buffer solution most preferable is an about 0.1M HEPES/HEPES salt buffer solution containing about 9.53 g/l of HEPES and about 15.62 g/l of HEPES salt and having a pH-value of about 7.7 at a temperature of 25° C. The buffer solution can be prepared by dissolving appropriate amounts of the base and its salt, e.g., of HEPES and of HEPES salt in deionized water.

It has been found advantageous to add from 1.2 to 2.2 mg/ml of ethylene maleic anhydride (EMA) as a stabilizer and adjuvant. A dose is one milliliter. Surprisingly it has been found that the presence of EMA acts as an adjuvant and potentiates the effectiveness of the vaccine.

The rabies vaccine composition according to the present invention is prepared and used in form of sterilized suspension of proteineous suckling mouse brain particles of injectable particle size laden with the inactivated rabies virus in the aqueous buffer solution having a slightly basic pH-value. The proteineous viral laden material will generally be suspended in the aqueous buffer solution such that the same will provide the virus in the final product in a concentration sufficient to provide the desired antigenic response.

While the invention is described using suckling mouse brain tissue, it is to be understood that suckling rat brain tissue may be substituted therefor.

Notwithstanding the fact that substantially any strain of mice or rats could be used to propagate the rabies virus useful in the vaccines of this invention, it was preferred that a strain known to be useful for medical purposes be used and most preferred that a germ-free strain be employed for propagation of the virus. A germ-free colony of suitable mice has been developed and the same is designated as Strain $CF_1$ by the supplier, Harlan Sprague Dawley, Madison, Wis.

The high virus titers are the result of the buffer composition of this invention. In this regard, it should be noted that these relatively high potencies will be consistently obtained when care is exercised to insure the high titers heretofore described and to insure that the final vaccine contains at least about 0.3 wt% of the viral laden brain tissue.

It has been found advantageous to add an indicator dye, such as phenol red, to facilitate the adjustment of the pH and to monitor the pH during inactivation and storage. Phenol red is added in a concentration of about 30 mg per liter or 0.003 percent by volume. The solution may be sterilized in accordance with well known methods, for example, by heating to a temperature of about 120° C. for about 30 to 60 minutes.

It has also been found advantageous to add preservatives, such as antibiotics, particularly polymyxin B, neomycin and amphotericin B, to the buffered solution. Alternatively the preservatives may be added to the suspension of proteineous viral laden particles when prepared.

The rabies vaccine may be prepared by the following procedure:
(a) suspending a sufficient amount of viral laden suckling mouse brain tissue material in a sterilized aqueous buffer solution of HEPES and its salt having a pH of between about 7.5 and about 8.0. to obtain a concentrated suspension of at least about 60% by weight of brain tissue material;

(b) comminuting the suspended virus laden brain material within the concentrated suspension into particles of injectable particle size;

(c) diluting the concentrated suspension with a sufficient amount of the sterilized aqueous buffer solution to obtain a dilute suspension wherein the concentration of the virus laden brain particles is no greater than about 17% by weight;

(d) inactivating the dilute suspension; and (e) adjusting the concentration of virus laden brain particles in the inactivated suspension to obtain the vaccine composition.

The preferred embodiment for the preparation of a rabies vaccine composition comprising a sterilized suspension of virus-laden proteinaceous suckling mice brain particles is as follows.

(a) Preparation of starting virus-laden suckling mice brain tissue material.

The rabies virus for vaccine production is propagated by injecting suckling mice intracerebrally at an age between two and four days with a working seed containing living, fully virulent rabies virus, which working seed is prepared by diluting a master seed to a virus titer between about 300 to 1000MLD$_{50}$ per dose. The master seed, in turn, is prepared by inoculating 2–4 day old suckling mice from the same source as that used for future propagation with a CVS strain rabies virus and then harvesting the viral laden brain tissue. The master seed has a virus titer of at least $10^{6.0}$MLD$_{50}$ per 0.01 ml at a concentration of 10 wt%. The production virus is then harvested from the inoculated mice after the development of typical rabies symptoms, when the mice have become moribund (4–5 days).

The virus-laden mouse brain tissue is mixed with a sufficient amount of the buffer solution to form a concentrated suspension, preferably containing between about 30 and about 60 wt% (percent by weight) of the virus laden brain tissue. Suitably, the buffer solution will contain the buffer composition and the preservatives required to make a final vaccine concentration between about 20 and 30 mcg (micrograms) of polymyxin B, 20 and 30 mcg of neomycin and between about 1 and 2.5 mcg of amphotericin B per milliliter of final vaccine product.

To reduce the size of the brain particles to a size suitable for injection the suspension is subjected to high shear agitation. The size of all particles is preferably about 1 to 10 microns.

The resulting suspension is stored at a temperature of about $-40°$ C. while quality control tests are completed prior to use. Typically the suspension is tested for purity, safety, and potency. For the preparation of a vaccine product, the suspension has a virus titer of at least $10^5$MLD$_{50}$ per 0.1 ml at a concentration of 0.35 wt% (for a one-year vaccine), and at least $10^6$MLD$_{50}$ per 0.1 ml at a concentration of 0.6 wt% (for a three-year vaccine).

When the virus laden brain tissue material to be used in the vaccine is frozen, it is rapidly thawed and then diluted with the buffer solution to a concentration ranging between about 4 and about 20 wt%. The diluted suspension of virus laden brain tissue particles is filtered to remove particles having a size greater than 10 microns.

Inactivation may be accomplished chemically with compounds such as $\beta$-propiolactone or formalin or the virus may be inactivated with ultraviolet light. Chemical inactivation with $\beta$-propiolactone is preferred because minimal antigenic distortion results.

An aqueous solution containing about 5 to 15 volume percent of unhydrolyzed $\beta$-propiolactone is prepared by dissolving a pharmaceutical grade of unhydrolyzed $\beta$-propiolactone in either distilled or deionized water. Typically, the unhydrolyzed $\beta$-propiolactone solution is prepared at a temperature of about 4° and 5° C. and then added to the diluted suspension at or near room temperature (22°–26° C.) so that the composite product contains $\beta$-propiolactone in a dilution within the range of about 1:1,000 and 1:10,000. The resulting composition product is maintained at room temperature and subjected to constant agitation for about 24 to 30 hours. During this period, the $\beta$-propiolactone hydrolyzes and the virus is inactivated. If necessary the pH-value may be readjusted to a range of between about 7.5 and 8.0 following inactivation. The vaccine has a storage life of at least 24 months at a temperature between about 4° and 5° C. under sterile conditions. The vaccine may be stored in a single or multiple dose containers. The vaccine is used in accordance with the well known techniques. Typically, a single dose will range between about 1 and 5 ml.

The rabies vaccine compositions prepared in accordance with the present invention exhibit a potency, as determined in mice, of at least ten times the NIH minimum standard. The increased potency is believed to be the result of the relatively high virus titers. The thus propagated virus is harvested and used only if there is no evidence of atypical rabies virus propagation and only if satisfactory results are obtained in all tests required by Federal Regulations such as those required by Title 9 of the code of Federal Regulations.

The virus laden mice are stored in aluminum containers at a temperature between about $-45°$ and $-70°$ C. When the mice are ready for processing, they are thawed at room temperature and by immersion in a tincture of iodine at a temperature of about 20° to 25° C. Once the mice have been thawed, yet still at about 4° C., the brains are withdrawn from the cranial cavity using a 14 gauge hypodermic needle inserted tangentially in the forward aspect of the cranial cavity in combination with a vacuum aspirator. After harvesting, the brains are pooled together.

(b) Preparation of rabies vaccine.

The pooled virus laden brain material is subsequently suspended in a 0.1 M (molar) solution of HEPES/HEPES salt containing a sufficient amount of antibiotics to provide protection up to 30 mcg of polymyxin B, up to 30 mcg of neomycin and up to 2.5 mcg amphotericin B per milliliter of final vaccine product as required by government regulations. In the preferred embodiment, the virus laden mouse brains are suspended, initially, at a concentration of about 15 wt% to 60 wt% and then subjected to high shear agitation so as to reduce the particle size of the suspended mouse brains to between about 1 and 10 microns.

Between about 2 and 10 ml of the suspension thus prepared are withdrawn and diluted for purposes of further tests. The remaining portion is stored at a temperature between about $-45°$ and $-70°$ C. and subsequently used in the preparation of a rabies vaccine after control test results are available.

In the preparation of the rabies vaccine, the concentrated about 15 to 60 wt% frozen suspension is thawed at a temperature of between 4° and 5° C. and diluted to a concentration of about 10 to about 20 wt%. Dilution is effected with an aqueous 0.1M solution of Hepes/Hepes salt buffer. The diluted suspension then is reground by high shear agitation and filtered under sterile conditions to remove particles greater than 10 microns. The pH of the resulting suspension is between about 7.5 and 7.8.

During the dilution, grinding, and filtration, the suspension is maintained at a temperature of between 15° and 25° C. Following the dilution, grinding, and filtration, the rabies virus is inactivated with a solution containing between about 5 and 15 wt% of unhydrolized β-propiolactone, such as Purified Fellows (Medical) Beta propiolactone. The β-propiolactone solution at 4°–5° C. is added to the diluted suspension at a temperature of between about 15° and 25° C. Best results are obtained when the β-propiolactone solution is added to the diluted suspension within five minutes after preparation thereof. The combined mixture will be allowed to become fully hydrolized by continuous agitation at room temperature for about 24 hours.

The concentration of suspended tissue in the product must be between about 0.3 and 5 wt% to insure standardization of the product. The product is suitable for packaging or may be stored under sterile conditions.

In order more clearly to disclose the nature of the present invention, specific examples of the practice of the invention are hereinafter given. It should be understood, however, that this is done solely by way of example and is intended neither to delineate the scope of the invention nor limit the ambit of the appended claims. Temperatures are expressed in degrees Celsius (°C.) and g indicates grams, ml indicates milliliters, l indicates liters, mcg indicates micrograms, wt% indicates percent by weight.

In the definition of the virus titer $10^{7.2}$ is a logarithmic expression which indicates the number of virus particles at the specified quantity and concentration of the mice brain suspension, that is, 15,848,932 virus particles. The term $MLD_{50}$ indicates the minimum lethal dose at which death loss of 50 percent of the mice occurs.

EXAMPLE 1

This example illustrates the preparation of virus laden suckling mice brain tissue starting material for a master seed suspension.

For preparing a concentrated suspension of living, fully virulent rabies virus, one 0.5 ml ampule of a 10 wt% lyophilized mouse brain suspension was obtained from the Bureau of Biologics, Dept. of H.E.W., Public Health Service, Food & Drug Administration, Rockville, Md., containing the CVS rabies virus strain originally isolated by Pasteur in 1882. (Fernandes et al., Virology 21, 128, 1963) The ampule was identified by Serial No. CVS-31B. The ampule was then pooled, reconstituted and diluted with 0.5 ml of distilled water containing 2% by volume horse serum which was further diluted to 1:1000. The 1:1000 virus dilution was used to intracerebrally inoculate three day old, suckling mice.

The stock breeders used to produce the mice which were inoculated in this and subsequent Examples were from the germ-free strain designated $CF_1$ and available from Harlan Sprague Dawley, Madison, Wis. These breeders were housed in an environment used solely for the purpose of producing a gnotobiotic colony of mice to be used to propagate the rabies virus useful in the vaccines of this invention.

The inoculation was accomplished with a 0.5 cc syringe with a 26 gauge, 3/8 inch long needle, inserted approximately midway into the cranial cavity at an adequate depth into one of the cerebral hemispheres and each of the inoculated mice received 0.03 ml of the viral suspension. The inoculated mice developed typical rabies symptoms after three days and became moribund starting the fourth day. The moribund, inoculated mice were then stored at a temperature of −50° C. The virus laden brain tissue was separated from the inoculated mice by first warming the frozen mice to a temperature of about 5° C., treating the skin surface of the inoculated mice with a 0.5% tincture of iodine and then withdrawing the brain by inserting a 14 gauge hypodermic needle tangentially in the forward aspect of the cranial cavity. The hypodermic needle was attached to a safety-trapped vacuum system which was closed between the harvest of each individual mouse brain. The brain tissue was withdrawn from the inoculated mice.

EXAMPLE 2

The procedure of Example 1 was repeated except that the moribund, inoculated mice instead of being frozen and stored, were cooled to 4° C. for continuous processing. This eliminated the steps of freezing, storing and thawing.

EXAMPLE 3

This example illustrates the preparation of a sterilized suspension medium.

A buffer solution was prepared by mixing 9.53 g/l HEPES, 15.62 g/l of HEPES sodium salt and 6.2 g/l sodium chloride in 1000 ml deionized water and 7.5 ml of 0.4% solution of phenol red. The pH of the solution was 7.7. The solution was sterilized by autoclaving at 121° C. for 30 minutes. The suspension medium was tested for sterility and found satisfactory for use in the preparation of vaccines and was stored under sterile conditions.

EXAMPLE 4

This example illustrates the preparation of a concentrated master seed suspension of virus laden suckling mice brain tissue.

The tissue, 6.4 grams, which was obtained as described in Example 1 was diluted to 10% tissue by volume with sterilized saline solution phosphate buffered to pH 7.2 and containing 2% by volume of horse serum. The solution also contained 50 mcg neomycin per milliliter, 50 mcg per milliliter of polymyxin B and 2 mcg amphotericin B per milliliter of suspension. The resulting suspension contained 10 wt% of the virus laden brain tissue and was subjected to high shear agitation in a Waring blender for a period of one minute so as to reduce the size of the brain particles to a size between about 1 and 10 microns. After removal of a sample for testing, the remainder of the 10 wt% solution was dispensed in 1.5 ml and 5 ml amounts into ampules and stored at −45° to −70° C.

The concentrated viral suspension of Step C was tested for purity, safety, potency, sterility and identity, as described in 9 CFR 113.129 Rabies Vaccines, Killed Virus. The virus titer of the suspension was found to be $10^{7.2} MLD_{50}$ per 0.01 ml thereof and the suspension was found to be satisfactory for use as a primary master seed.

EXAMPLE 5

This example illustrates the preparation of virus laden suckling mice brain tissue starting material for a vaccine composition:

A one milliliter portion of the master seed obtained in Example 4 was thawed and diluted with a sterilized, phosphate buffered, saline solution containing 2% normal horse serum to provide a suspension of living, fully virulent rabies virus having a virus titer between 300 and 1000MLD$_{50}$ per 0.03 ml thereof. A 0.03 ml portion of this suspension was then injected intracerebrally into 1120 two-to four-day old, suckling mice. Starting the third day, the inoculated mice developed typical rabies symptoms and all of the inoculated mice became moribund starting the fourth day. The moribund mice were frozen on day 4 post inoculation and stored at $-50°$ C. until further processed. Then 1014 mice were thawed and the living, fully virulent rabies virus harvested by removal of the brain tissue from the mice in the same manner as that set forth in Example 1. After separation, the brains from the mice were pooled yielding 190.3 grams.

The viral laden brain tissue was then suspended in a sterilized, 0.1M solution of HEPES/HEPES sodium salt buffer further containing, 360 mcg of neomycin, 360 mcg polymyxin B and 18 mcg amphotericin B per ml thereof. A suspension was prepared containing 60 wt% of the virus laden mice brain tissue in the buffer solution.

The 60 wt% suspension was subjected to high shear agitation in a homogenizer at a temperature of 5° C. so as to reduce the size of the brain tissue to a value of between 1 and 10 microns. Five milliliters (5 ml) was then removed for quality control testing and the remainder stored at $-50°$ C. The suspension was tested for potency. The 60 wt% suspension was found to have a virus titer of $10^{6.7}$MLD$_{50}$ per 0.03 ml and to be satisfactory for use in the preparation of a three-year rabies vaccine.

EXAMPLE 6

This example illustrates the preparation of inactivated rabies vaccine compositions.

After satisfactory results were obtained in the quality control tests, the concentrated 60 wt% viral laden mouse brain suspensions obtained in Example 5 was thawed by warming to a temperature range of 20°–25° C. and then diluted and reground in a Waring blender to 16.67 wt% suspensions by diluting with the buffer solution prepared in Example 3. The diluted suspension was maintained at 20°–25° C. and was aseptically filtered through a 305 mesh nylon membrane utilizing positive air pressure within a closed container to remove particles having a particle size greater than 10 microns. The living, fully virulent viruses contained in the remaining portion of the dilute suspension was inactivated with a solution containing 10 wt% of β-propiolactone. The β-propiolactone solution was prepared by adding a medicinal grade of unhydrolyzed β-propiolactone (Fellows Medical) at a temperature of $-20°$ C. to deionized water at a temperature of 5° C. and the mixture was agitated to dissolve the solute. The β-propiolactone solution was transferred to the diluted suspension with sterile, filtered air pressure at a rate of 5.0 ml per liter of diluted suspension in an amount providing a 1:2000 dilution of β-propiolactone in the combined product.

The suspension was then placed in a 20°–25° C. incubator and stirred continually for a period of 24 hours.

The vaccines were packaged in a plurality of single and 10 dose vials. The final vaccine product contained at least 0.3 wt% of the viral laden mouse brain tissue extracted from the suckling mice and used in the preparation of the vaccine for a one-year immunization period and 0.6 wt% for a three-year immunization period in dogs and cats. The packaging was accomplished in sterile conditions into suitable containers. Each of the single dose bottles contained 1.1 ml of the vaccine and the 10 dose bottles contained 11.0 ml each.

EXAMPLE 7

The vaccine compositions obtained in Example 6 were tested for inactivation by inoculating 0.03 ml intracerebrally into mice 21 days old. In one series of tests, 10 mice were injected with the vaccine composition as prepared. All the mice survived the entire 21 day observation period thus indicating that the rabies virus in the vaccine had been inactivated.

EXAMPLE 8

The relative potency or antigenic factor of the vaccine prepared in Example 6 was determined in accordance with the procedure set forth for the Modified National Institute of Health potency test, which procedure is summarized in the World Health Organization "Laboratory Techniques in Rabies" 2nd Edition, 1966. The materials and methods used, and results obtained are as follows:

Test samples were diluted to 16.67% wt with the buffer solution according to the present invention which had been prepared by mixing 9.53 g/l of the HEPES with 15.62 g/l of the HEPES sodium salt and 6.2 g/l of sodium chloride. Phenol red was added to the solutions at a concentration up to 7.5 mls/l of a 0.4% by volume solution.

The test suspension was inactivated with β-propiolactone at a concentration of 1:2000 for a 24-hour period carried out at room temperature (22°–23° C.). The pH of the HEPES/HEPES salt buffered suspension was buffered at a pH of 7.7 throughout the inactivation procedure.

The pH of the test suspension was maintained at 7.8 during the inactivation period, by adding 1N KOH (one normal potassium hydroxide solution) as necessary.

At the end of the 24-hour inactivation period, samples were aseptically drawn with a serological pipet and tested for the presence of live virus using the mouse safety test. Dilutions of 1:1, 1:10 and 1:100 were inoculated into 10 mice for each dilution of the test suspension and observed for 21 days. No rabies deaths attributable to live virus were observed.

An amount of 16.67% v/v (percent volume per volume) stabilizer was added to the test suspensions that was further diluted as described in Example 6 to obtain a test vaccine. The stabilizer employed was pharmaceutical grade ethylene maleic anhydride (EMA), obtained from Monsanto. The EMA was prepared as a 1% concentration and added to the vaccine at 16.67% v/v to provide a final stabilizer content of 0.1667 g/l in the vaccine compositions.

The completed test vaccine composition was thoroughly mixed by agitation for 0.5 hours after the addition of the stabilizer and samples of the completed test vaccine composition was taken for safety and potency testing. The vaccine was incubated at 37° C. for 336 hours and the potency of the lot tested, using the NIH potency test, after completion of the final product to determine the antigenic value of the experimental lot. The antigenic values obtained from the NIH potency after incubation of the sample is listed in Table 1, where $EPD_{50}$ means median Effective Protective Dose, which is that dose which protects fifty percent of the mice challenged.

TABLE 1

Antigenic Values of Rabies Vaccine Formulated Hepes/Hepes sodium salt Buffered Saline and Phosphate Buffered Saline.

| Antigenic Value Before Incubation of Vaccine | | Antigenic Value After Incubation of Vaccine | |
|---|---|---|---|
| $EPD_{50}$ Test Vaccine | 428 | $EPD_{50}$ Test Vaccine | 216 |
| $EPD_{50}$ Ref. Vaccine | 60 | $EPD_{50}$ Ref. Vaccine | 29 |
| Antigenic Value | 7.1 | Antigenic Value | 7.4 |

The antigenic value is determined by dividing the $EDP_{50}$ of the test vaccine by the $EDP_{50}$ of the reference vaccine.

The results from the above test suspensions confirmed that the stability of the virus was maintained by the HEPES/HEPES salt buffered suspensions after the addition of β-propiolactone.

Results of the safety test in mice revealed no rabies deaths attributable to live virus in all groups tested.

The foregoing Examples clearly indicate that the vaccines of this invention are safe and effective for the purpose intended. The rabies vaccine prepared in accordance with this invention did produce immunity in both dogs and cats to this disease.

What is claimed is:

1. A rabies vaccine composition comprising a sterilized suspension of at least about 0.3% by weight of proteinaceous suckling mice or rat brain particles of injectable particle size laden with inactivated rabies virus, in an aqueous buffer solution having a slightly basic pH value and an amount, dissolved therein, of a buffer composition sufficient to stabilize the pH at said value, said buffer composition comprising a mixture of an organic base of between 0.02 and 0.08 moles per liter, of a buffer composition comprising an organic base formula

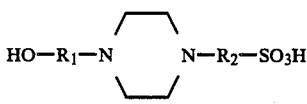

wherein $R_1$ and $R_2$ are $CH_2$, $C_2H_4$ or $C_3H_6$, combined with an acid addition salt thereof, which is compatible with virus replication.

2. A rabies vaccine composition comprising a sterilized suspension of proteinaceous suckling mice or rat brain particles of injectable particle size laden with an amount of inactivated rabies virus which is equivalent to a virus titer of from at least about $10^5$ to about $10^6 MLD_{50}$ per 0.1 milliliter thereof, at a brain tissue concentration of from about 0.7 to about 1.2% by weight, in an aqueous buffer solution having a pH between about 7.5 and about 8.0 and comprising an amount dissolved therein of about 0.02 to 0.08 moles per liter, of a buffer composition comprising of an organic base formula

wherein $R_1$ and $R_2$ are $CH_2$, $C_2H_4$ or $C_3H_6$, combined with about 0.03 and 0.12 moles per liter of an acid addition salt thereof.

3. The rabies vaccine composition as defined in claim 2, wherein the buffer composition comprises a mixture of N-2 hydroxyethylpiperazine-N-2 ethanesulfonic acid and its sodium salt.

4. The rabies vaccine composition as defined in claim 3, wherein in the buffer composition the weight ratio of N-2 hydroxyethylpiperazine-N-2 ethanesulfonic acid and its sodium salt is from about 1.0/1.0 to 1.0/4.0.

5. The rabies vaccine composition as defined in claim 4, wherein the weight ratio is about 15.62/9.53.

6. The rabies vaccine composition as defined in claim 2, wherein said aqueous buffer solution is a 0.04 molar solution of said buffer composition.

7. The rabies vaccine composition as defined in claim 2, wherein said brain particles are laden with an amount of said inactivated rabies virus which is equivalent to a virus titer of from at least about $10^5$ to about $10^6 MLD_{50}$ per 0.1 milliliter of said suspension.

8. The rabies vaccine composition as defined in claim 2, wherein the particle size of the brain particles is between about 1 and about 10 microns.

9. The rabies vaccine composition as defined in claim 2, wherein the organic base is N-2-hydroxyethylpiperazine-N-3 propane sulfonic acid.

10. The rabies vaccine composition as defined in claim 2 which comprises between about 0.7 to 1.2 percent by weight of brain particles.

11. The rabies vaccine composition as defined in claim 2 in which the amount of brain particles is about 1.2 percent by weight.

12. The rabies vaccine composition as defined in claim 2 further containing an adjuvant.

13. The rabies vaccine composition as defined in claim 12 where said adjuvant is ethylene maleic anhydride.

14. The rabies vaccine composition as defined in claim 13 where said ethylene maleic anhydride is present in the amount of 1.2 to 2.2 mgs per dose.

15. A veterinary rabies vaccine composition comprising an effective amount of a rabies virus antigen, a pharmaceutically acceptable carrier and an effective amount of ethylene maleic anhydride.

* * * * *